US009039666B2

(12) United States Patent
Voss et al.

(10) Patent No.: US 9,039,666 B2
(45) Date of Patent: May 26, 2015

(54) METHOD AND APPARATUS FOR LIQUID DISPENSING (71) Applicant: Johnson & Johnson Vision Care, Inc., Jacksonville, FL (US)

(72) Inventors: Leslie A. Voss, Jacksonville, FL (US); Catie A. Morley, St. Johns, FL (US); Gary S. Hall, St Johns, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 6 days.

(21) Appl. No.: 13/632,912

(22) Filed: Oct. 1, 2012

(65) Prior Publication Data

US 2013/0085460 A1 Apr. 4, 2013
US 2015/0005721 A9 Jan. 1, 2015

Related U.S. Application Data (63) Continuation-in-part of application No. 13/600,105, filed on Aug. 30, 2012, and a continuation-in-part of application No. 12/902,575, filed on Oct. 12, 2010, now abandoned, and a continuation-in-part of (Continued)

(51) Int. Cl.
*A61F 9/00* (2006.01)
*A61M 11/00* (2006.01)

(52) U.S. Cl.
CPC ............ *A61M 11/005* (2013.01); *A61F 9/0026* (2013.01); *A61F 9/0008* (2013.01); *A61M 2205/50* (2013.01); *A61M 2205/8206* (2013.01); *A61M 11/007* (2014.02)

(58) Field of Classification Search
CPC .... A61F 9/0008; A61F 9/0026; A61M 11/00; A61M 11/005; A61M 11/007; A61M 2205/50; A61M 2205/8206
USPC .................................. 604/289–290, 294–300
See application file for complete search history.

(56) References Cited

U.S. PATENT DOCUMENTS

| 4,952,212 | A | 8/1990 | Booth et al. |
| 4,992,808 | A | 2/1991 | Bartky et al. |
| 5,171,306 | A | 12/1992 | Vo |
| 5,368,582 | A | 11/1994 | Bertera |
| 5,894,841 | A | 4/1999 | Voges |
| 6,039,056 | A * | 3/2000 | Verbeek ..................... 134/22.18 |
| 6,210,000 | B1 | 4/2001 | Yee |

(Continued)

FOREIGN PATENT DOCUMENTS

| EP | 1493410 A2 | 1/2005 |
| WO | WO 9952479 A2 | 10/1999 |

(Continued)

OTHER PUBLICATIONS

PCT International Search Report, dated Jan. 31, 2011, for PCT Int'l Appln. No. PCT/US2010/053132.

(Continued)

*Primary Examiner* — Philip R Wiest
*Assistant Examiner* — Benjamin Klein (57) ABSTRACT This invention provides for a method and a device for dispensing precise quantities of a predetermined volume of medicaments or other liquids onto the eye, via one or more discrete drop(s) generated by the device in a practical and innoxious way to users.

24 Claims, 6 Drawing Sheets

Related U.S. Application Data application No. 12/902,603, filed on Oct. 12, 2010, now abandoned.

(60) Provisional application No. 61/541,349, filed on Sep. 30, 2011, provisional application No. 61/529,627, filed on Aug. 31, 2011, provisional application No. 61/253,613, filed on Oct. 21, 2009, provisional application No. 61/256,111, filed on Oct. 29, 2009.

(56) References Cited

U.S. PATENT DOCUMENTS

| | | | |
|---|---|---|---|
| 6,270,467 B1 | 8/2001 | Yee | |
| 8,012,136 B2 * | 9/2011 | Collins et al. | 604/298 |
| 2003/0135169 A1 | 7/2003 | Cohen et al. | |
| 2004/0039355 A1 | 2/2004 | Gonzalez et al. | |
| 2004/0204674 A1 * | 10/2004 | Anderson et al. | 604/66 |
| 2005/0001981 A1 | 1/2005 | Anderson et al. | |
| 2007/0211212 A1 | 9/2007 | Bennwik | |
| 2008/0173545 A1 | 7/2008 | Anex et al. | |
| 2008/0233053 A1 | 9/2008 | Gross et al. | |
| 2010/0076388 A1 * | 3/2010 | Cater | 604/298 |
| 2010/0145529 A1 * | 6/2010 | Thomason et al. | 700/283 |
| 2011/0092925 A1 | 4/2011 | Voss et al. | |
| 2011/0106025 A1 | 5/2011 | Hall et al. | |
| 2011/0152913 A1 | 6/2011 | Jones et al. | |

FOREIGN PATENT DOCUMENTS

| | | |
|---|---|---|
| WO | WO 9952479 A3 | 10/1999 |
| WO | WO 2004028421 A1 | 4/2004 |

OTHER PUBLICATIONS

PCT International Search Report, dated Jan. 17, 2011, for PCT Int'l Appln. No. PCT/US2010/053144.

* cited by examiner

METHOD AND APPARATUS FOR LIQUID DISPENSING

CROSS REFERENCE TO RELATED APPLICATIONS

The present application claims priority to U.S. Provisional Patent Application No. 61/541,349, filed Sep. 30, 2011 entitled "Method and Apparatus for Liquid Dispensing". This present application is also a Continuation-in-Part of and claims priority to the following applications: (1) U.S. Non-Provisional application Ser. No. 13/600,105, filed Aug. 30, 2012 entitled "Liquid Dispensing Reservoir", which claims priority to U.S. Provisional Patent Application No. 61/529,627, filed Aug. 31, 2011 entitled "Liquid Dispensing Reservoir"; (2) U.S. Non-Provisional patent application Ser. No. 12/902,575, filed on Oct. 12, 2010 entitled "Liquid Dispensing With Blink Detection", which claims priority to U.S. Provisional Patent Application No. 61/253,613, filed Oct. 21, 2009 entitled "Liquid Dispensing with Blink Detection"; and (3) U.S. Non-Provisional application Ser. No. 12/902,603 filed on Oct. 12, 2010 entitled "Ophthalmic Fluid Pump", which claims priority to U.S. Provisional Application No. 61/256,111, filed Oct. 29, 2009 entitled "Ophthalmic Fluid Pump". The contents of which these applications are relied upon and incorporated herein by reference.

FIELD OF USE

This invention describes a device for dispensing precise quantities of liquids in one or more discrete drop(s), vapor, or mists onto a surface of an eye, more specifically, the device being capable of generating one or more discrete drop(s) for the optimal administration of a predetermined dose.

BACKGROUND OF THE INVENTION

It has been known to dispense a liquid or a mist into an eye using many different devices. However, although many devices result with a liquid entering the eye, the experience of getting the liquid into the eye and the dosage precision administered by the user of the devices is generally less than satisfactory.

Devices for self-dispensing liquids into the eye typically require that a user hold the eyelids open to fight the blink reflex. This contention not only inhibits easy application of the desired fluids, but also results in inconsistent dosage to the eye. Some automated devices pull down on one lid, or encapsulate the eye area to stop the lids from closing. This touch is damaging to makeup, and may lead to contamination of the device and the liquid entering the eye.

The dose from the system should consistently, without great user effort, dispense into the user's eye, not upon the eyelid or other part of the users face, and optimally should not touch the face in a manner that damages makeup or contaminates the device.

Some dispensing devices simulate a 'gun' and shoot a fluid in at the eye at a rate calculated to beat the blink reflex, however the speed and impact of the fluid often induce discomfort to the patient.

Other devices force the lids open in different manners through touching the cheek below the lid, and the eyebrow range above the upper lid, then spray the fluid into the eye. This forcing open of the lids is uncomfortable, and the unit itself becomes large and unwieldy. Any makeup worn by the consumer is smudged during the process and sometimes contaminates the dispenser and/or the dispensed liquid.

Misting of fluid over the entire eye or even the facial area is also feasible, but doing so wets not only the eye, but also undesirable surfaces such as the eyelid, forehead, and nose resulting in uncertainty regarding the actual dose administered. Application of liquid to the eyelid is declared to also wet the eye by flowing into the eye, but results from this method are mixed, and the wetting of the lid itself is typically undesirable and unpredictable.

SUMMARY OF THE INVENTION

Accordingly, the present invention includes an eye medicament-dispensing unit (sometimes referred to herein as "EMDU") for dispensing one or more precise quantities of medicaments or other liquids onto a surface of an eye via one or more of: a discrete drop, a mist, and a vapor without creating significant discomfort. More specifically, the apparatus of the present invention discloses an EMDU that is capable of consistently dispensing droplets to create one or more discrete drop(s) of pre-determined volumes of liquid during a critical time window, for optimal innoxious dose administration.

In some embodiments, the present invention automatically senses a blink or other external condition and dispenses the liquid in a timely fashion based upon the external condition. For example, a microcontroller may receive a signal that a blink has occurred and time administration of a liquid following the blink to allow the liquid to enter the eye before the eye may blink again. By using the window just after the blink, the present invention consistently provides enough time to dispense into the eye and also dispense at a rate which is an adequately slow application of fluid into the eye to maintain the inertial impact of the fluid on the eye at a comfortable level.

DETAILED DESCRIPTION OF THE INVENTION

The present invention provides for an eye liquid dispensing device used to provide precise dosage administration without significant discomfort to the user. In the following sections detailed descriptions of embodiments of the invention will be given. The description of both preferred and alternative embodiments though thorough are exemplary embodiments only, and it is understood that to those skilled in the art that variations, modifications, and alterations may be apparent. It is therefore to be understood that the exemplary embodiments do not limit the broadness of the aspects of the underlying invention as defined by the claims.

GLOSSARY

In this description and claims directed to the presented invention, various terms may be used for which the following definitions will apply:

"Discrete Drop" as used herein, refers to a quantity of fluid that generally falls in one spherical mass characterized by distinct or individual parts.

"Jet Dispensing" as used herein and sometimes referred to "Dispensing", refers to a non-contact administration process that utilizes a fluid jet to form one or more droplet(s) of liquid and expel them from the Dispensing Tip accordingly.

"Pull Back" as used herein, refers to the decompression or pull-back due to a pressure difference. For example, in most conventional medical grade vented containers, the pressure difference created when dispensing a liquid from the container would result in Pull Back.

"Pump" as used herein, refers to an EMDU used to transfer liquid by pumping action. May be driven with motors, solenoids, and/or air pressure.

"Valve" as used herein, refers to a device that controls or regulates the flow of liquid/material from a reservoir, to the dispensing tip by opening and closing a passageway. For example, a passive valve.

"Viscosity" as used herein, refers to the measure of a liquid's resistance to deformation under mechanical stress. Viscosity is a function of fluid temperature and usually decreases as temperature increases.

"Voids (entrapped air)" as used herein, refers to air bubbles due to Pull Back in the vessel, reservoir, or feed channels to the dispensing tip that may cause inaccuracies of quantities dispensed and contamination of the liquid.

DESCRIPTION

The present invention pertains to an EMDU for Dispensing liquids onto the Ophthalmic Environment of a user, in a practical way that does not cause significant discomfort to the user. In order to achieve this, the EMDU must be capable of timely dispensing a liquid dose in a fairly horizontal trajectory and in predetermined small volume droplets to avoid discomfort. Additionally, the device must be portable, use low power and may respond to a signal, for example a signal resulting from the detection of a blink, within 100 milliseconds for effectiveness in the administration of the liquid onto the user's eye.

Figure 1:
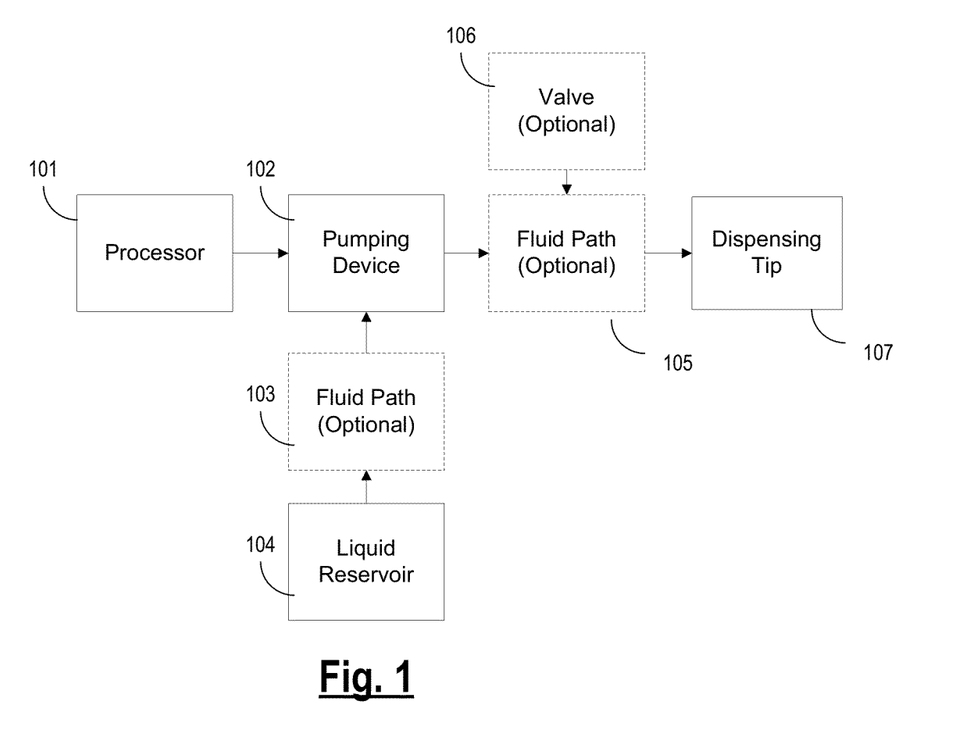
FIG. 1 illustrates a simplified schematic diagram of an electronic droplet generator that may be used in the present invention.

Referring now to FIG. 1, a simplified schematic diagram of an electronic droplet generator that may be used in the present invention is depicted. At 101, a processor capable of sending a signal to a Pump 102 correlated to one or more events that can produce optimal administration is depicted. Said signal's shape, amplitude, frequency, voltages and dosing time are which are the pump parameters influencing the Jet Dispensing behavior. Amplitude and frequency together are the main parameter to drive the pump and adjust flow rate. Varying both parameters may result that higher frequencies and higher voltages lead to better jet dispensing performances, meaning for example, a very stable jet dispensing with no separate droplets, low pulsation and a clean start and stop.

Figure 2:
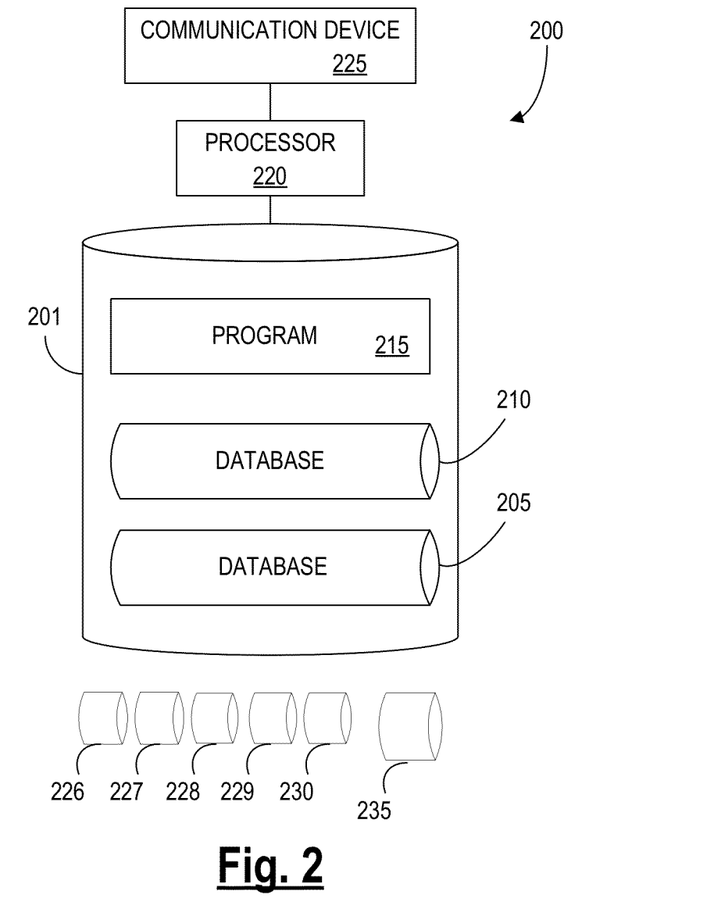
FIG. 2 illustrates a simplified schematic diagram of an exemplary microcontroller that may be used in the apparatus of the present invention.

In FIG. 2 a simplified schematic diagram of an exemplary microcontroller 200 that may be used in some embodiments of the present invention is depicted. The microcontroller 200 includes a processor 210, and one or more processor components and/or support function circuitry 226-230 such as a crystal oscillator, timers, watchdog timer, serial and analog I/O etc.; program memory in the form of NOR flash or OTP ROM is also often included, as well as some amount of RAM.

The microcontroller 200 may also include a communication device 225. In some embodiments, a microcontroller 200 can be used to receive a logical indication that an eye is in a first state or a second state and transmit energy to the Pump at a time appropriate to dispense a liquid into the eye, based upon the transition from a first state to a second state. Other logic may also be programmed into the microcontroller and provide for flexibility of function. By way of non-limiting example, such functionality may include monitoring how much fluid is currently stored in one or both of the reservoir and liquid fluid path; duration of pump actuation which correlates into a precise amount of liquid administered to the eye, which reservoir is being drawn from; periodic timing of liquid disbursement; duration of liquid disbursement and almost any other functionality related to the operation of the Pump.

The one or more processors can be coupled to a communication device 225 configured to communicate energy via a communication channel. The communication device may be used to electronically control, for example, one or more of: timing of liquid dispensing; an amount of liquid dispensed; duration of a dispensing motion; tracking a number of dispensing actions; tracking chronological dispensing patterns or other actions related to the dispensing.

The processor 220 may also be in communication with a storage device 201. The storage device 201 may comprise any appropriate information storage device, including for example: semiconductor memory devices such as Random Access Memory (RAM) devices and Read Only Memory (ROM) devices.

The storage device 201 can store a program 215 for controlling the processor 220. The processor 220 performs instructions of the program 215, and thereby operates in accordance with the present invention. For example, the processor 220 may receive information descriptive of liquid to be dispensed, dispensing amounts, dispensing patterns, and the like to generate one or more droplet(s) for administration onto a surface of the eye.

In addition, the present invention may include an Energy Source 235, such as an electrochemical cell or battery as the storage means for the energy and in some embodiments, encapsulation, and isolation of the materials comprising the Energy Source from an environment into which an ophthalmic pump is placed. The Energy Source 235 can provide power to activate the microcontroller. In some embodiments, power consumption of a microcontroller while sleeping (CPU clock and most peripherals off) may be just nanowatts.

Figure 3:
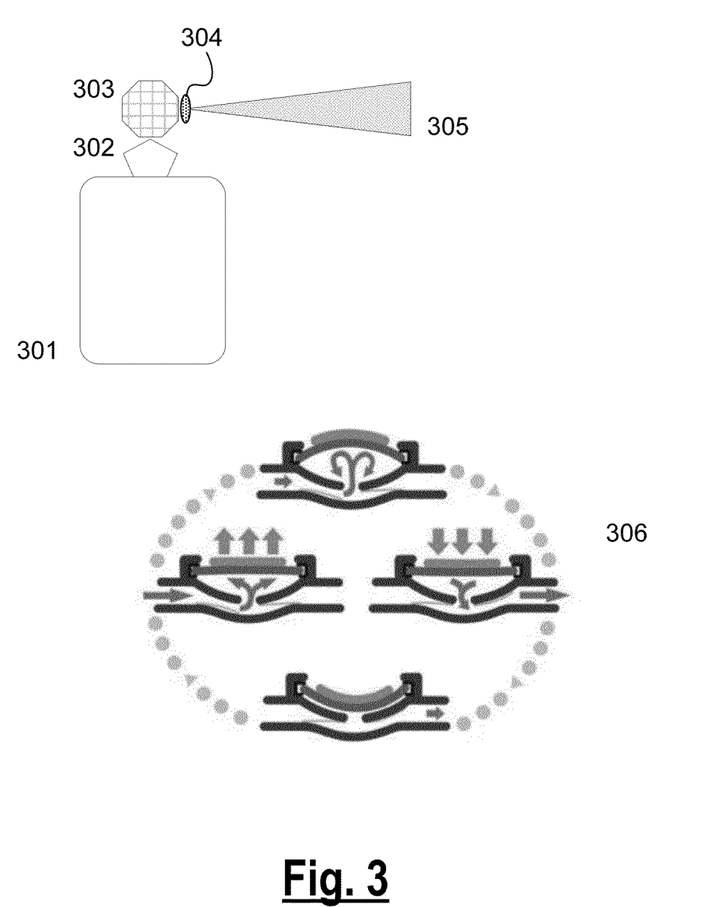
FIG. 3 illustrates an exemplary Pump that may be used in the apparatus of the present invention.

Referring back to FIG. 1 the processor 101 is in logical connection with a pumping device 102 that may be used in the present invention. Respectively, FIG. 3 depicts an exemplary pumping device 102 for liquid dispensing to an eye. The pumping device which may include a main reservoir 301, a dosing reservoir 302, an electrically controlled pumping mechanism 303, and a Dispensing Tip 304. When the pumping mechanism 303 is activated, it may draw from one or both of the main reservoir 301 and the dosing reservoir 302 to pump a liquid discrete drop 305 into a surface of an eye.

The main reservoir 301 can contain a liquid to be dispensed into the eye. The liquid can include, for example, a solution useful for treating dryness or other condition in the eye, a medicament, a nutrient, or other substance efficacious to the eye.

In some embodiments, a single dose reservoir 302 may be included. Other embodiments work directly from the main reservoir 302. The single dose reservoir 302 is in liquid communication with the main reservoir 301 and may be filled with an amount generally equal to a single dose of liquid to be administered to the eye.

The pump may draw from one or both of the single dose reservoir 302 and the main reservoir 301. The Pump can include a piezo electric pump, a diaphragm type pump, a positive displacement type pump or other device capable of pumping specific amounts of a liquid into a surface of an eye. In some preferred embodiments, a piezo electric type pump generally used to administer specific amounts of liquid on a regular basis, such as for example, a piezo electric pump used to pump pharmaceuticals into a an intravenous feed, may be adapted to pump a liquid from one or both of the reservoirs 301-302, through the Dispensing Tip. Typically, a pharmacy administering pump would need to be adapted to pump with a shorter duration and higher pressure action in order to provide the pulsatile delivery required to administer a liquid to an eye by a discrete drop. This is a change from the constant low speed, but tightly controlled amounts fed into an intravenous feed. Some specific examples can include the MP5 and MP6 offered by Bartels Mikrotechnik GmbH.

A functional diagram of how a micropump may operate is also included 306.

Specifications may include, for example:
Pump type piezoelectric diaphragm pump
Number of actuators 2
Dimensions without connectors 30×15×3.8 mm$^3$
Weight 2 g
Fluidic connectors tube clip (outer diameter 1.6 mm, length 3.5 mm)
Electric connector flex connector/Molex FCC 1:25 mm pitch
Power consumption <200 mW
Self-priming yes 2
Pumping media liquids, gases and mixtures
Operating temperature 0-70° C. 3
Life time 5000 h 3
IP code IP33 4
Materials in contact with media polyphenylene sulphone (PPSU)
Suitable evaluation controller mp-x and mp6-OEM
Typical values of flow and back pressure for selected media (values defined with mp-x: 250 V, SRS):
Gases Max. flow on request
Max. back pressure on request
Liquids Water Max. flow 6 ml/min+/−15% (100 Hz)
Max. back pressure 550 mbar+/−15% (100 Hz)

Additional examples of pump specifications may include:
Pump type piezoelectric diaphragm pump
Number of actuators 1
Dimensions without connectors 14×14×3.5 mm$^3$
Weight 0.8 g
Fluidic connectors tube clip (outer diameter 2 mm, length 3 mm)
Electric connector flex connector/phone jack
Power consumption <200 mW
Self-priming yes 2
Pumping media liquids or gases
Operating temperature 0-70° C.
Life time 5000 h 3
IP code IP44
Materials in contact with media polyphenylene sulphone (PPSU),
polyimide (PI), nitrile butadiene
rubber (NBR)
Suitable evaluation controller mp-x and mp5-a
Typical values of flow and back pressure for selected media (values defined with mp-x: 250 V, SRS):
Gases Max. flow 15 ml/min (300 Hz)
Linear range 0-5 ml/min @0-50 Hz
Max. back pressure 30 mbar (300 Hz)
Liquids Water Max. flow 5 ml/min (100 Hz)
Linear range 0-3 ml/min @0-30 Hz
Max. back pressure 250 mbar (100 Hz)
Repeatability
(30 Hz, 250 V, SRS)
<12%
Viscosity <~120 mPas
1 Typical values. Values can vary under application conditions. Conditions: suction pressure <10 mbar, DI water, settings mp-x: 100 Hz, 250 V, SRS, the max. flow rate can be reached by manual priming. 3 Conditions: DI water, room temperature, settings mp-x: 100 Hz, 250 V, SRS.

In some preferred embodiments, the pump will provide enough pressure to dispense the liquid into the surface of an eye from a distance of about 15 millimeters (mm) without causing significant discomfort. Distances may therefore be between about 5 mm and 45 mm. In addition, an amount of spray should be controllable within about 5 micro liters of accuracy in amounts of between 3 and 30 micro liters, and preferably about 15 micro liters.

According to some embodiments of the present invention, the detector is placed in logical communication with the automated pump 303 capable of dispensing a predetermined amount of a liquid through the eye orifice nozzle and into the eye surface.

Referring back to FIG. 1, a fluid path 103 may be included in the apparatus depending on the assembly. The fluid path 103 may exist between the liquid reservoir 104 and the pumping device 102 all the way to the Dispensing Tip. It can comprise things such as one or more valves to prevent significant Suck Back and/or Voids that may result in inaccuracies and contamination of the liquid medicament in some embodiments. The fluid path may be medical grade polyethylene ("PE") tubing. However, the length may influence the performance of the apparatus depending on different parameters, such as the Pump and Valves used, Viscosity of the liquid dispensed, etc. In some embodiments, tubing length may be critical since longer tubing may result in undefined stops of the liquid causing weaker dispensing and therefore inaccuracies when hitting the target area, i.e. the desired surface of the eye. The reason for this can be explained by a too low pressure which may be needed to propel the fluid out of the nozzle, but this may be overcome by using a more powerful pump. However, if this is the case it must also be considered that the expansion of the tubing depending on the material used due to the pressure or the tiny but existent liquid compression inside of it may also cause inaccuracies. A solution in some embodiments to overcome this is to shorten the tubing length as it may be appropriate or to have no tubing but instead the Dispensing Tip 107 be directly plugged to the outlet of the pumping device 102.

In some embodiments, the Dispensing Tip 107 of the apparatus maybe syringe steel needles of different diameters which may depend on the Viscosity of the liquid, frequencies and amplitudes used for the signal to the pumping device, and the desired volume of the discrete drop. It is also assumed to be obvious to those skilled in the art that disturbances like, for example scratches or deformations in the needle tip heavily influence the jet performance causing unstable dispensing and/or satellite drops to appear. An example of a Dispensing Tip 107 that may be used in some embodiments of this invention is a tapered PE or steel needle with a diameter from 200-400 μm. Additionally, Tapered nozzles may be superior than straight tunnels in the standard syringe needles depending on the frequencies and amplitudes used, as higher frequencies and higher amplitudes may be better for distinct Jet Dispensing.

In some embodiments the device includes features to minimize the need for facial contact during liquid application. Additional embodiments include alignment features to assure proper alignment of the device to the eye. For example, in some embodiments, the dispensing device includes protrusions that rest on the eyebrow, and have a small diameter hole for the user to look through. When the user is able to see through the hole, proper alignment has been achieved.

Once the device is properly aligned with an eye, opening and closing of the eye is automatically determined by a sensor. A dispensing apparatus in logical communication with the sensor is programmed to dispense a liquid or mist into the eye according to the timing of an open cycle of a blink. The alignment process coupled with the blink detection eliminates the need for holding the lids open, touching the face, or contamination associated with regular facial touch. In addition, by dispensing based upon an opening motion of an eyelid, a dispenser according to the present invention, consistently wets the eye without wetting the eyelid or surrounding face.

Figure 4:
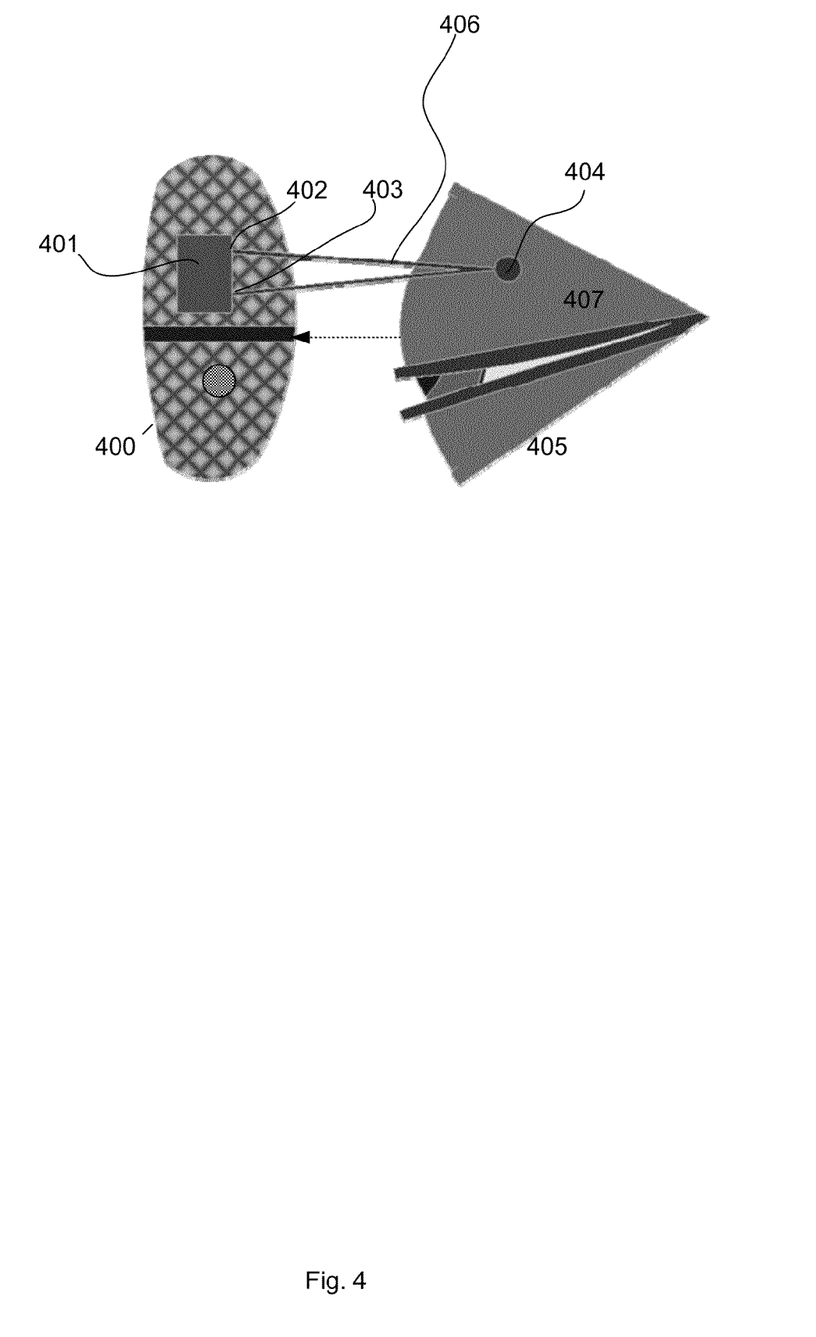
FIG. 4 illustrates a dispensing device sensing a closed eye according to some embodiments of the present invention.

Referring now to FIG. 4, in some embodiments, a liquid dispensing device 400 includes a sensor 401 capable of sensing an open state or a closed state of an eye 405. In some embodiments, the sensor 401 includes an emitter 402 and a detector 403. The emitter 402 emits a beam 406 which reflects off of a reflecting point 404 and back to the detector 403. As illustrated in FIG. 4, the reflecting point 404 is on the eyelid 407 of the eye. The beam 406 may include, for example one or more of: infra-red light, visible light, ultrasonic wavelengths, or other wavelengths.

Figure 5:
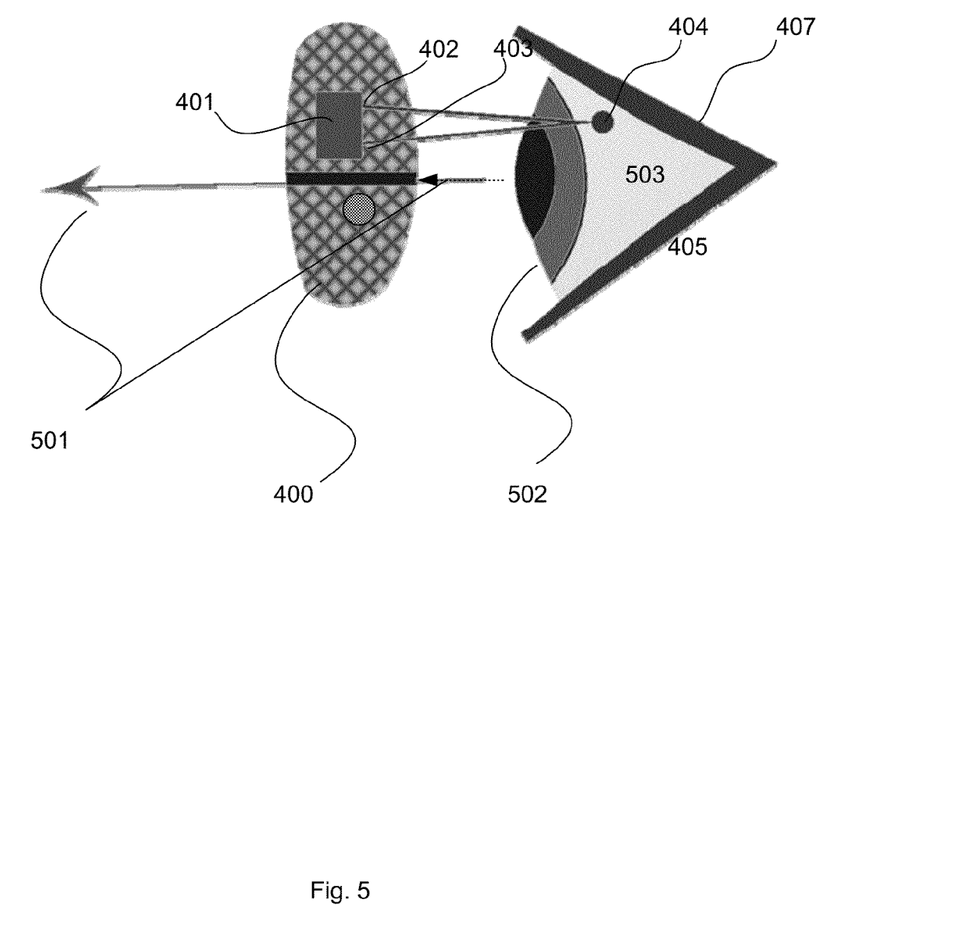
FIG. 5 illustrates a dispensing device sensing an open eye according to some embodiments of the present invention.

Referring now to FIG. 5, an open eye 405 provides for a reflecting point 404 on an open portion 503 of the eye 405, as opposed to the eyelid 407. The open portion of the eye 503 can include, for example, reflection off of the sclera or other portion of the eye. In some embodiments, a wavelength of an emitted beam is correlated with physical characteristics of the reflecting point 404. Reflection of the emitter beam 406 off of the eyelid will reflect back with a first set of reflection characteristics and reflection off of the open portion of the eye 503 with a second set of reflection characteristics. The reflection characteristics will be sensed by the detector 403.

In another aspect, of the present invention, alignment of the eye 405 with the liquid dispensing device 400 is facilitated by the liquid dispensing device. According to the present invention, a focal point of the emitter 402 is aligned with a predetermined portion of the eye, such as, for example: the sclera, iris, and pupil of the eye. Alignment can be accomplished, for example, via a line of sight 501. In some embodiments, when a pupil 502 is aligned with the line of sight 501, the sensor 401 is also properly aligned to sense an open state and a closed state of the eye 405. For example, in some embodiments, when a patient aligns to a tubular cutout comprising a line of sight 501 in the dispensing device, it creates a coaxial alignment between the line of sight and the center of the tube. The alignment establishes an angular and X-Y location of the pupil relative to the dispensing device 400, wherein X-Y correlate to a vertical and horizontal planar position at a given distance from the eye.

In some embodiments, a line of sight can be combined with a positioning device which includes one or more alignment legs which press against the face and/or forehead. In addition, in some embodiments, a sensor measures the distance of the device from the eye and signals (perhaps by click, sound, or vibration) that it is within an acceptable Z positional range from the eye for an optimal dose wherein the Z dimension correlates with a depth or distance from the eye.

Figure 6:
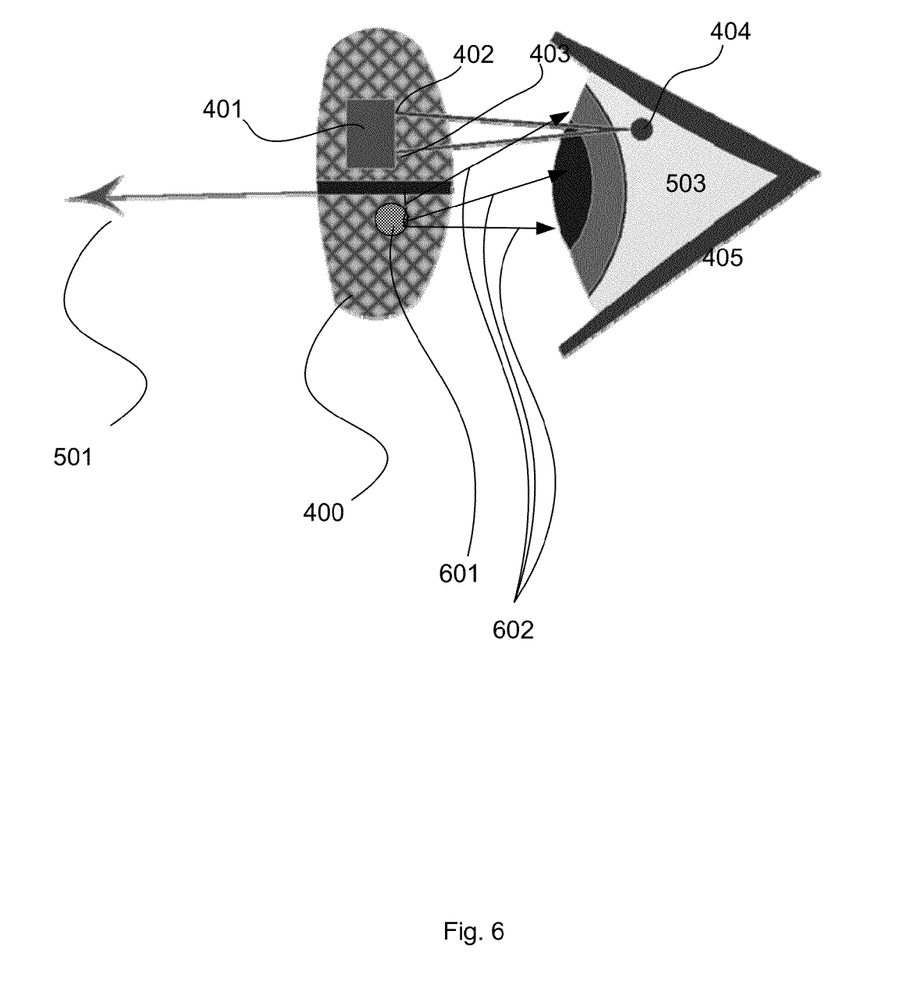
FIG. 6 illustrates an exemplary apparatus for sensing a state of an open or closed eye.

Referring now to FIG. 6, a dispensing nozzle 601 will dispense a liquid via sprays 602 or mist (not illustrated) when the sensor 401 senses that the eye 405 is in an open state. The open state is determined by the nature of the beam 406 sensed by the detector 403. Preferred embodiments, dispense a liquid spray 602 based upon timing that indicates that the eyelid 407 is involved in an opening cycle. Dispensing sprays 602 during an opening cycle of an eye can be accomplished such that the patient cannot physically blink to close the eye before the liquid is dispensed. The spray may be a liquid stream or a mist.

CONCLUSION

The present invention, as described above and as further defined by the claims below, provides apparatus and methods of providing a method and apparatus being capable of generating one or more discrete drop(s) for the optimal administration of a predetermined dose without discomfort to the user.

The invention claimed is:

1. An apparatus for dispensing a liquid into an ophthalmic environment comprising:
    an emitter configured to emit radiation of a predetermined wavelength in a direction towards an eye;
    a sensor configured to detect the wavelength of radiation reflected from the eye, wherein the reflected wavelength will be different based upon whether the eye is in an open state or a closed state;
    an automated dispenser configured to dispense 3 to 30 microliters of the liquid towards the eye from a distance of 5 to 45 millimeters based upon receipt of a logic signal from a processor that is in logical communication with at least the sensor and the automated dispenser,
    a steerable nozzle dispensing tip in fluid communication with the automated dispenser to jet dispense and in logical connection with the sensor to minimize manual adjustment by a user,
    wherein the processor also transmits the logic signal based upon an electrical signal from the sensor indicating whether the eye is in the open state or the closed state to the automated dispenser,
    wherein the automated dispenser is further configured to respond to the logic signal within 100 milliseconds of the state determination; and
    wherein the reflected wavelength is indicative of a proper alignment of the apparatus with a predetermined ophthalmic region of the eye.

2. The apparatus of claim 1, wherein the automated dispenser is further configured to dispense the liquid based upon receipt of the logic signal associated with the eye being in the open state and in the proper alignment with the automated dispenser.

3. The apparatus of claim 1, wherein the logic signal coordinates dispensing of the liquid towards the eye in a horizontal trajectory.

4. The apparatus of claim 1, wherein the emitter and sensor comprise a camera.

5. The apparatus of claim 4, wherein the camera comprises an infrared camera.

6. The apparatus of claim 5, wherein the infrared camera further comprises an infrared filter.

7. The apparatus of claim 1, additionally including a digital storage storing executable software operative with the processor to cause the processor to be configured to coordinate dispensing of the liquid towards a predetermined ophthalmic region of the eye based upon the wavelength of the reflected radiation.

8. The apparatus of claim 7, wherein the dispensing of the liquid is based upon receipt of a signal indicating the predetermined ophthalmic region is aligned.

9. The apparatus of claim 1, additionally comprising a feedback signaling device in electrical communication with the sensor, wherein the feedback signaling device is configured to be activated based upon a signal from the sensor.

10. The apparatus of claim 9, wherein the feedback signaling device is an audible signaling device emitting audible signals to a user for an alignment.

11. The apparatus of claim 9, wherein the feedback signaling device is a visual signaling device providing a visual signal to a user for an alignment.

12. The apparatus of claim 11, wherein the dispensing of the liquid is further based upon the receipt of a signal indicating the eye is in the open state.

13. The apparatus of claim 9, wherein the feedback signaling device is a sensory signaling device configured to provide a change for sensory nerves of a user for an alignment.

14. The apparatus of claim 9, wherein the feedback signaling device comprises a combination of an audible and a visual signal.

15. The apparatus of claim 1, wherein the dispensing of the liquid is in predetermined volumes of one or more droplets.

16. The apparatus of claim 1, wherein the liquid is at least one of: a discrete drop, a mist, and a vapor.

17. The apparatus of claim 1, additionally comprising a single dose reservoir and a main reservoir, wherein the single dose reservoir is in communication with said main reservoir and may be filled with approximately a single dose of the liquid to be dispensed upon receipt from the logic signal.

18. The apparatus of claim 1, additionally comprising a tubular cutout, wherein the tubular cutout is configured to coaxially align with a line of sight of a user when the apparatus is in the proper alignment with the predetermined ophthalmic region of the eye.

19. The apparatus of claim 1, additionally comprising a positioning device, wherein the positioning device includes at least one alignment leg that presses against a face or a forehead of a user to aid in the proper alignment of the apparatus.

20. The apparatus of claim 1, wherein the automated dispenser is further configured to dispense a first portion of a desired volume of the liquid in a first dispensing action based on a first eye-open state determination and dispense a remaining portion of a desired volume of the liquid in a second dispensing action based on a second eye-open state determination.

21. The apparatus of claim 20, wherein the second eye-open state determination follows an eye-closed state determination.

22. The apparatus of claim 20, additionally comprising a pump, wherein the processor is further capable of sending an additional logic signal to the pump based on the first portion of the desired volume of the liquid dispensed during the first dispensing action.

23. The apparatus of claim 22, wherein the additional logic signal regulates the pump and adjusts a flow rate of the liquid.

24. The apparatus of claim 23, wherein the additional logic signal includes at least one of: a signal shape, an amplitude, a frequency, a voltage, and a dosing time.

* * * * *